(12) United States Patent
Heeney et al.

(10) Patent No.: US 7,524,922 B2
(45) Date of Patent: *Apr. 28, 2009

(54) POLY(BENZODITHIOPHENES)

(75) Inventors: Martin Heeney, Southampton (GB); Clare Bailey, Southampton (GB); Steven Tierney, Southampton (GB); Weimin Zhang, Southampton (GB); Iain McCulloch, Southampton (GB)

(73) Assignee: Merck Patent Gesellschaft Mit Beschrankter Haftung, Darmstadt (DE)

( * ) Notice: Subject to any disclaimer, the term of this patent is extended or adjusted under 35 U.S.C. 154(b) by 417 days.

This patent is subject to a terminal disclaimer.

(21) Appl. No.: 10/963,720

(22) Filed: Oct. 14, 2004

(65) Prior Publication Data

US 2005/0082525 A1 Apr. 21, 2005

(30) Foreign Application Priority Data

Oct. 15, 2003 (EP) .................................. 03023339

(51) Int. Cl.
*C08G 61/12* (2006.01)
*C07D 495/02* (2006.01)

(52) U.S. Cl. .................. 528/380; 528/377; 549/43; 257/40; 257/E51.029; 257/E51.036; 257/E51.05; 428/917; 313/504

(58) Field of Classification Search ................ None
See application file for complete search history.

(56) References Cited

U.S. PATENT DOCUMENTS 6,913,710 B2 * 7/2005 Farrand et al. ......... 252/299.61

FOREIGN PATENT DOCUMENTS

| EP | 1300430 A1 | 4/2003 |
|---|---|---|
| EP | 1357163 A1 | 10/2003 |
| JP | 10-340786 | * 12/1998 |
| JP | 11322906 | 11/1999 |

OTHER PUBLICATIONS

Machine-assisted translation of JP 10-340786 (Dec. 1998).*
Pomerantz et al., "Poly(benzo[1,2-b:4,5-b']dithiophene-4,8-diylvinylene) . . . ", Macromolecules, vol. 27, No. 25, pp. 7478-7485 (1994).*
Patent Abstracts of Japan, Feb. 29, 2000, vol. 2000, No. 2 & JP 11 322906, Yamamoto Ryuichi, Nov. 26, 1999, abstract.
Shiraishi, K. et al., "New π-conjugated polymers constituted of dialkoxybenzodithiophene units: synthesis and electronic properties," Synthetic Metals, 2002, p. 139-147, vol. 130, Elsevier Science.

* cited by examiner

*Primary Examiner*—Marie R. Yamnitzky
(74) *Attorney, Agent, or Firm*—Millen, White, Zelano & Branigan, P.C.

(57) ABSTRACT

Disclosed are novel poly(benzodithiophenes), their use as semiconductors or charge transport materials in optical, electro-optical or electronic devices, for example, liquid crystal displays, optical films, organic field effect transistors (FET or OFET) for thin film transistor liquid crystal displays and integrated circuit devices such as RFID tags, electroluminescent devices in flat panel displays, and in photovoltaic and sensor devices, and to a field effect transistor, light emitting device or ID tag.

24 Claims, 3 Drawing Sheets

POLY(BENZODITHIOPHENES)

FIELD OF INVENTION

The invention relates to novel poly(benzodithiophenes). The invention further relates to their use as semiconductors or charge transport materials, in optical, electro-optical or electronic devices like for example liquid crystal displays, optical films, organic field effect transistors (FET or OFET) for thin film transistor liquid crystal displays and integrated circuit devices such as RFD tags, electroluminescent devices in flat panel displays, and in photovoltaic and sensor devices. The invention further relates to a field effect transistor, light emitting device or ID tag comprising the novel polymers.

BACKGROUND AND PRIOR ART

Organic materials have recently shown promise as the active layer in organic based thin film transistors and organic field effect transistors [see H. E. Katz, Z. Bao and S. L. Gilat, *Acc. Chem. Res.*, 2001, 34, 5, 359]. Such devices have potential applications in smart cards, security tags and the switching element in flat panel displays. Organic materials are envisaged to have substantial cost advantages over their silicon analogues if they can be deposited from solution, as this enables a fast, large-area fabrication route.

The performance of the device is principally based upon the charge carrier mobility of the semi-conducting material and the current on/off ratio, so the ideal semiconductor should have a low conductivity in the off state, combined with a high charge carrier mobility ($>1\times10^{-3}$ cm$^2$ V$^{-1}$ s$^{-1}$). In addition, it is important that the semi-conducting material is relatively stable to oxidation i.e. it has a high ionization potential, as oxidation leads to reduced device performance.

One of the best semi-conducting polymers currently available is regioregular poly(alkyl)thiophene (PAT), with a mobility around 0.1 cm$^2$V$^{-1}$s$^{-1}$. For example, regular poly(3-hexylthiophene) has been reported with a high charge carrier mobility between $1\times10^{-5}$ and $4.5\times10^{-2}$ cm$^2$ V$^{-1}$ s$^{-1}$, but with a rather low current on/off ratio between 10 and $10^3$ [see Z. Bao et al., *Appl. Phys. Lett.* 1997, 78, 2184]. In general, poly(3-alkylthiophenes) show improved solubility and are able to be solution processed to fabricate large area films. However, poly(3-alkylthiophenes) have relatively low ionization potentials and are susceptible to doping in air [see H. Sirringhaus et al., *Adv. Solid State Phys.* 1999, 39, 101].

Figure 1:
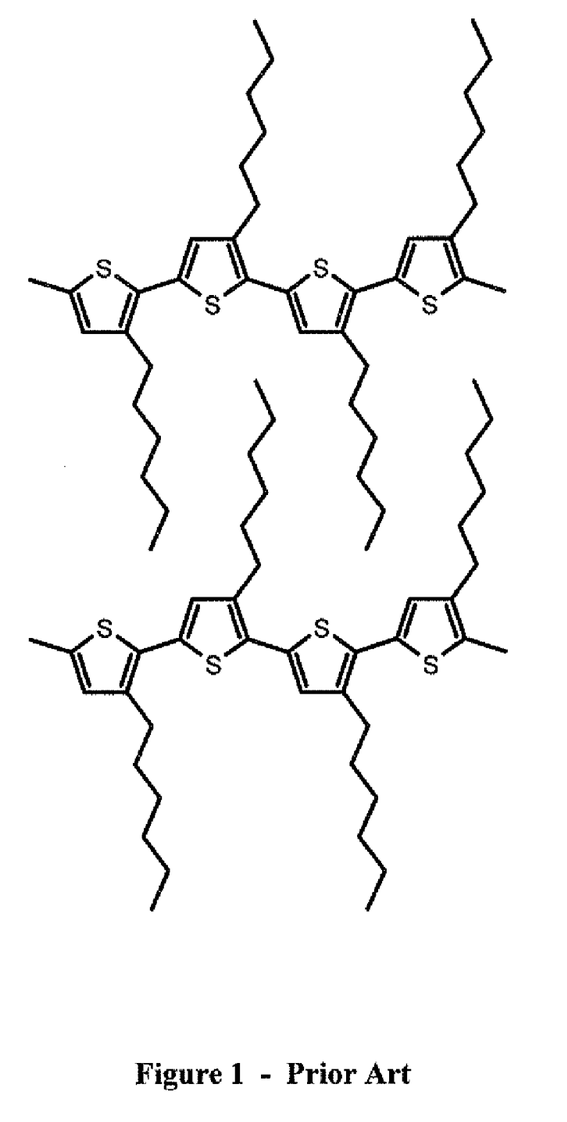
FIG. 1: illustrates the polymer chains of regioregular PAT being able to pack via interdigitation of their side-chains.

There are a number of features in PAT that contribute to its high charge carrier mobility. Firstly, the polymer chains of regioregular PAT are able to pack via interdigitation of their side-chains, as schematically depicted in FIG. 1. The side-chains are necessary to provide polymers that are soluble. This results in the formation of lamellar sheets of polymers, such a arrangement is beneficial to the charge-hopping mechanism with which charge is carried in organic materials [see P. J. B. H. Sirringhaus, R. H. Friend, M. M. Nielsen, K. Bechgaard, B. M. W. Langeveld-Voss, A. J. H. Spiering, R. A. J. Janssen, E. W. Meijer, P. Herwig & D. M. de Leeuw, *NATURE*, 1999, 401, 685]. Secondly, PAT contains an abundance of sulfur atoms in the thiophene rings. The presence of sulfur atoms has been shown to be beneficial to charge transport, the exact mechanism is not known, but it is speculated that interaction of the sulfur d-orbitals on adjacent polymer chains facilitates the charge hopping mechanism. The major drawback of PAT, however, is that the material is oxidatively unstable. This means that the material chemically degrades in the presence of oxygen, leading to low shelf stability, and secondly the material is susceptible to doping by oxygen which results in high transistor off currents and poor transistor performance. The oxidative instability of PAT is due to the presence of many electron-rich thiophene rings in the polymer backbone, which results in a high HOMO level (around −4.9 eV).

Incorporation of benzodithiophene units in a PAT-backbone results in a polymer backbone that is less electron rich than the equivalent all-thiophene polymer, since benzene is much less electron rich thiophene.

Benzo[1,2-b:4,5-b']dithiophene, hereinafter also shortly referred to as benzodithiophene or BDT, with the following structure (1)

(1)

has been reported in the literature to have a high charge carrier mobility and to be useful as organic semiconductor. BDT monomers or dimers, oligo- or polymers formed thereof and their use as an organic semiconductor have been described for example in Kossmehl et al., *Makromol. Chem.* 1983, 184(3), 627-50, Katz et al., *J. Mater. Chem.* 1997, 7(3), 369-76, Laquindanum et al., *Adv. Mater.* 1997, 9(1), 36-39 and in U.S. Pat. No. 5,625,199. For example, bis(benzodithiophene) (2) is stable up to 400° C. in air [see H. E. Katz; Z. Bao; S. L. Gilat, *Accounts of Chemical Research*, 2001, 34, 359].

(2)

In particular the dimeric bisbenzodithiophene (2) has been shown to exhibit high charge carrier mobilities of 0.04 cm$^2$V$^{-1}$s$^{-1}$. Its structure has flatter conformation than e.g. α-sexithiophene with comparable size. This enables compressed molecular packing and strong intermolecular interactions, which is favorable for compact stacking of the material and results in π-π-overlap and hence makes this compound an effective charge transport materials with high carrier mobilities. However, bisbenzodithiophene has a very high melting point over 400° C. and very low solubility in organic solvents, so that it cannot be readily solution processed and can only be vacuum deposited.

To date some example's of a poly(benzodithiophene) substituted in the 4,8 positions have been reported. Shiraishi and Yamamoto reported polymers and co-polymers based upon alkoxy substituted BDT (3) [see K. Shiraishi; T. Yamamoto, *Synthetic Metals*, 2002, 130, 139-147].

(3)

R = CH$_3$ or C$_6$H$_{13}$

However, these polymers were poorly soluble and were only investigated as potential conductive materials after doping. Only alkoxy substituted polymers were described, however, these are undesirable for semiconducting materials since the electron donating alkoxy groups results in an increase of the HOMO level of the polymer, and subsequent stability problems. Additionally the routes described to these polymers are not amenable to the synthesis of the alkyl substituted polymers described here. Pomerantz et al reported a polymer whereupon benzodithiophene was polymerized through the 4,8 positions [see M. Pomerantz; J. Wang; S. Seong; K. P. Starkey; L. Nguyen; D. S. Marynick, *Macromolecules*, 1994, 27, 7478-7485]. However, no examples of alkyl substituted polymers or co-polymers have been described.

It was an aim of the present invention to provide new organic materials for use as semiconductors or charge transport materials, which are easy to synthesize, have high charge mobility and good processability. The materials should be easily processable to form thin and large-area films for use in semiconductor devices. In particular the materials should be oxidatively stable, but retain or even improve the desirable properties of PAT. Another aim of the invention was to provide BDT materials that are more easily processible in the manufacture of semiconductor devices, are stable and allow easy synthesis also at large scale.

It was found that the above aims can be achieved by providing poly(benzodithiophenes) according to the present invention. These polymers still possess alkyl chains perpendicular to the polymer backbone that are able to both solubilize the polymer in organic solvents and additionally are able to form closely packed interdigitated structures. Two positions are available for the alkyl chains in the BDT polymers according to this invention: substitution in 4,8-position (3) or substitution in 3,7-position (4).

(3)

(4)

Figure 2:
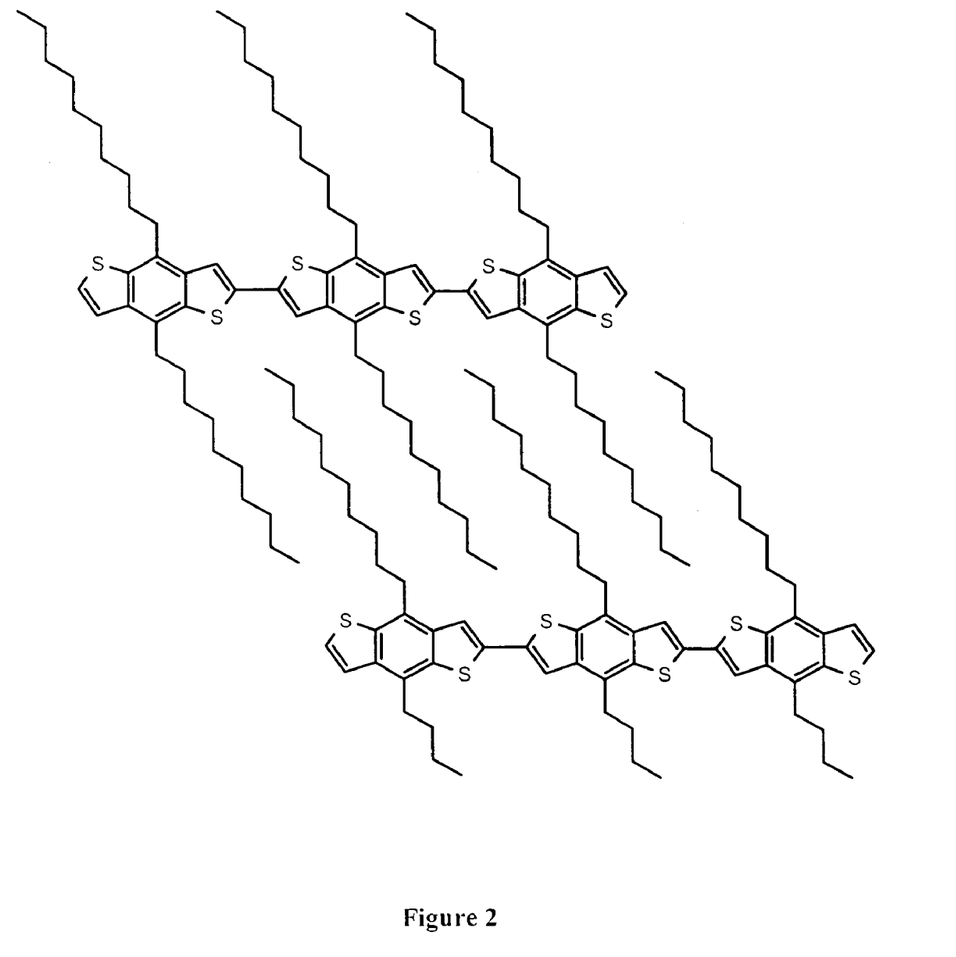
FIG. 2: illustrates a homo-polymer substituted in the 4,8 positions.
Figure 3:
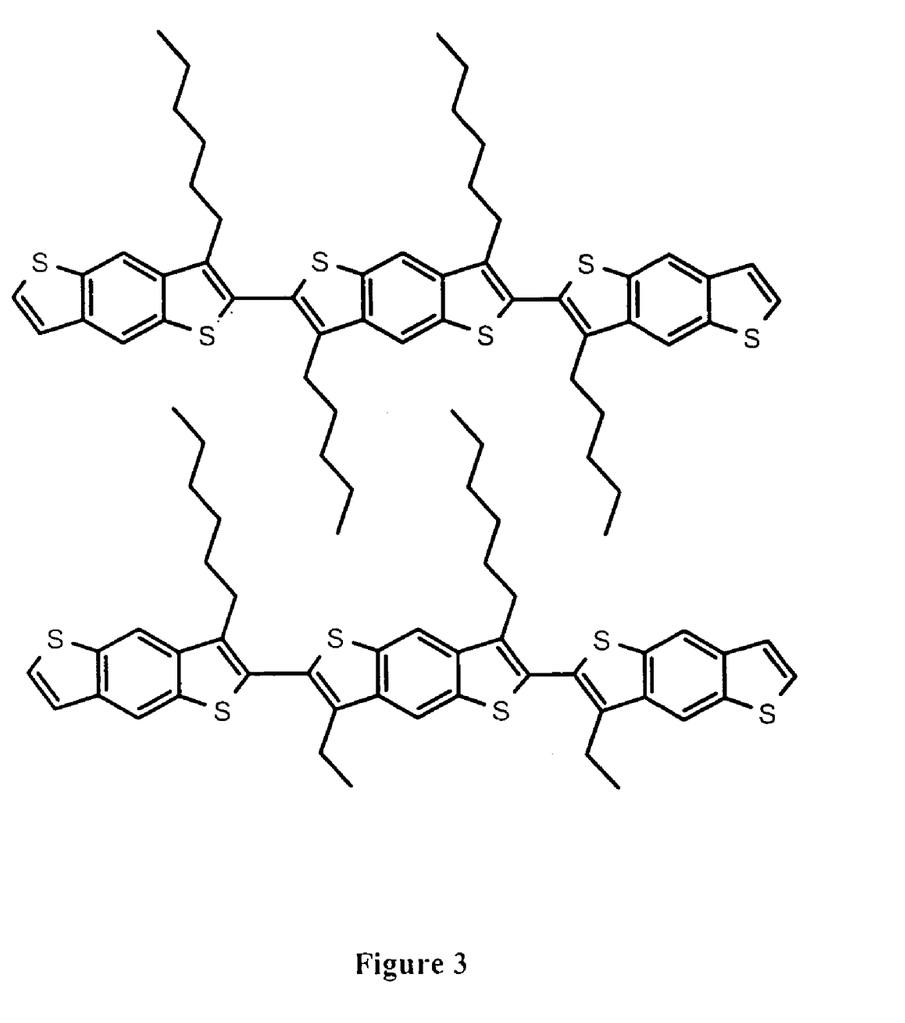
FIG. 3: illustrates a polymer substituted in the 3,7- positions.

Both these positions can afford closely packed structures, as schematically depicted in FIG. 2 for the homo-polymer substituted in the 4,8 positions and in FIG. 3 for the polymer substituted in the 3,7-positions. Furthermore, like PAT, the benzodithiophene polymers have sulfur atoms in the polymer backbone. An additional advantage of the poly(benzodithiophenes) according to the present invention is that the monomers from which the polymers are synthesized are symmetrical, therefore there are no problems regarding the regio-regularity of the resulting polymer. This simplifies the synthesis.

SUMMARY OF THE INVENTION

The invention relates to mono-, oligo- or polymers comprising at least one benzodithiophene (BDT) group that is substituted in 3- and 7-position and/or in 4- and 8-position, with the proviso that mono-, oligo- and poly(4,8-bisalkoxy-benzodithiophenes) are excluded.

The invention further relates to a semiconductor or charge transport material, component or device comprising at least one mono-, oligo- or polymer as defined above.

The invention further relates to the use of polymers according to the invention as semiconductors or charge transport materials, in particular in optical, electrooptical or electronic devices, like for example in field effect transistors (FET) as components of integrated circuitry, as thin film transistors in flat panel display applications or for Radio Frequency Identification (RFID) tags, or in semiconducting components for displays or organic light emitting diodes (OLED), including both the charge transport and electroluminescent layers.

The invention further relates to the use of the novel mono-, oligo- and polymers according to the present invention as electroluminescent materials, for OLED applications such as electroluminescent displays or backlights of displays, in photovoltaic or sensor devices, as electrode materials in batteries, as photoconductors, for electrophotographic applications like electrophotographic recording, for organic memory devices, for detecting and discriminating DNA sequences, and as alignment layer in LCD or OLED devices.

The invention further relates to an optical, electrooptical or electronic device, FET, integrated circuit (IC), TFT, OLED or alignment layer comprising a semiconducting or charge transport material, component or device according to the invention.

The invention further relates to a TFT or TFT array for flat panel displays, radio frequency identification (RFID) tag, electroluminescent display or backlight comprising a semiconducting or charge transport material, component or device or a FET, IC, TFT or OLED according to the invention.

The invention further relates to a security marking or device comprising a FET or an RFID tag according to the invention.

DETAILED DESCRIPTION OF THE INVENTION

The mono-, oligo and polymers according to the invention are especially useful as charge transport semiconductors in that they have high carrier mobilities. Particularly preferred are polymers wherein the BDT group is substituted by one or more alkyl or fluoroalkyl groups. The introduction of fluoroalkyl and alkyl side chains into the BDT group improves their solubility and therefore their solution processibility. Furthermore, the presence of fluoroalkyl side chains also renders these materials effective as n-type semiconductors. The electron-withdrawing nature of the fluoroalkyl substituents will also lower the HOMO further and result in a more stable material, which is less susceptible to oxidation.

Copolymerization of BDT with functionalized aromatic or unsaturated comonomers can further improve the solubility and the charge transport properties. Variation of the aromatic comonomers provides a method of tailoring the band gap of the polymers. This will lead to better stability and higher charge carrier mobility.

Particularly preferred are mono-, oligo- and polymers comprising one or more identical or different recurring units of formula I wherein
$R^1$ to $R^4$ are independently of each other H, halogen or straight chain, branched or cyclic alkyl with 1 to 20 C-atoms, which may be unsubstituted, mono- or poly-substituted by F, Cl, Br, I or CN, it being also possible for one or more non-adjacent $CH_2$ groups to be replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, or P-Sp-,
P is a polymerizable or reactive group,
Sp is a spacer group or a single bond,
$R^0$ and $R^{00}$ are independently of each other H or alkyl with 1 to 12 C-atoms, and
$Ar^1$ and $Ar^2$ are independently of each other —CX$^1$=CX$^2$—, —C≡C—, an arylene or heteroarylene group that is optionally substituted with one or more groups $R^1$, or a single bond,
$X^1$ and $X^2$ are independently of each other H, F, Cl or CN,
with the provisos that
a) in at least one recurring unit $R^1$ and $R^2$ are different from H and/or $R^3$ and $R^4$ are different from H,
b) $R^1$ and $R^2$ do not at the same time denote an alkoxy group.

Particularly preferred are mono-, oligo-, and polymers of formula I1 wherein $R^1$, $R^2$, $R^3$, $R^4$, $Ar^1$ and $Ar^2$ have independently of each other one of the meanings of formula I, n is an integer ≧1, preferably from 1 to 10,000, and wherein the recurring units may be identical or different.

The mono-, oligo-, and polymers of formula I1 are preferably selected of formula I1a wherein $R^1$, $R^2$, $R^3$, $R^4$, $Ar^1$, $Ar^2$ and n have independently of each other one of the meanings of formula I,
$R^5$ and $R^6$ are independently of each other H, halogen, —Sn(R$^0$)$_3$, —B(OR')(OR"), —CH$_2$Cl, —CHO, —CH=CH$_2$, —SiR$^0$R$^{00}$R$^{000}$, optionally substituted aryl or heteroaryl or P-Sp-,
$R^{000}$ has one of the meanings of $R^0$ in formula I,
R' and R" are independently of each other H or alkyl with 1 to 12 C-atoms, or OR' and OR" together with the boron atom form a cyclic group having 2 to 20 C atoms, and
P, Sp, $R^0$ and $R^{00}$ have the meanings of formula I.

Especially preferred are mono-, oligo-, and polymers of formula I, I1 and I1a having identical recurring units.

Further preferred are mono-, oligo-, and polymers of formula I, I1 and I1a wherein $R^1$ and $R^2$, or $R^3$ and $R^4$, respectively, are identical groups.

Especially preferred are oligo-, and polymers of formula I, I1 and I1a having a degree of polymerization (number n of recurring units) from 2 to 5000, in particular from 10 to 5000, very preferably from 100 to 1000.

Further preferred are mono-, oligo-, and polymers of formula I, I1 and I1a having a molecular weight (Mw) from 5000 to 300,000, in particular from 20,000 to 100,000.

Especially preferred are regioregular polymers of formula I, I1 and I1a, in particular with a high regioregularity of head-to-tail (HT) couplings. For example, in case of 3,7-substituted polyBDTs, the polymers preferably exhibit a high degree of HT-couplings of the following type The regioregularity in these polymers is preferably at least 90%, in particular 95% or more, very preferably 98% or more, most preferably from 99 to 100%.

Regioregular polymers are advantageous as they show strong interchain pi-pi-stacking interactions and a high degree of crystallinity, making them effective charge transport materials with high carrier mobilities.

Further preferred are mono-, oligo- and polymers of formula I, I1 and I1a comprising at least one reactive group P that is capable of a polymerization or crosslinking reaction.

Further preferred are mono-, oligo- and polymers of formula I, I1 and I1a that are mesogenic or liquid crystalline, in particular polymers forming calamitic phases, and reactive mesogens of formula I, I1 and I1a comprising one or more groups P-Sp-, forming calamitic phases.

Further preferred are mono-, oligo- and polymers of formula I, I1 and I1a shown above and below wherein Ar$^1$ and/or Ar$^2$ is thiophene-2,5-diyl that is optionally substituted, one of Ar$^1$ and Ar$^2$ is a single bond, both Ar$^1$ and Ar$^2$ are a single bond, Ar$^1$ and/or Ar$^2$ is CX$^1$=CX$^2$, n is an integer from 2 to 5000 and R$^1$, R$^2$, R$^3$ and R$^4$ are different from P-Sp-, R$^1$ and R$^2$ are selected from C$_1$-C$_{20}$-alkyl that is optionally substituted with one or more fluorine atoms, C$_1$-C$_{20}$-alkenyl, C$_1$-C$_{20}$-alkynyl, C$_1$-C$_{20}$-thioalkyl, C$_1$-C$_{20}$-silyl, C$_1$-C$_{20}$-ester, C$_1$-C$_{20}$-amino, C$_1$-C$_{20}$-fluoroalkyl, and optionally substituted aryl or heteroaryl, very preferably C$_1$-C$_{20}$-alkyl or C$_1$-C$_{20}$-fluoroalkyl, very preferably with R$^3$ and R$^4$ being H, R$^3$ and R$^4$ are selected from C$_1$-C$_{20}$-alkyl that is optionally substituted with one or more fluorine atoms, C$_1$-C$_{20}$-alkenyl, C$_1$-C$_{20}$-alkynyl, C$_1$-C$_{20}$-thioalkyl, C$_1$-C$_{20}$-silyl, C$_1$-C$_{20}$-ester, C$_1$-C$_{20}$-amino, C$_1$-C$_{20}$-fluoroalkyl, and optionally substituted aryl or heteroaryl, very preferably C$_1$-C$_{20}$-alkyl or C$_1$-C$_{20}$-fluoroalkyl, very preferably with R$^1$ and R$^2$ being H, R$^1$ and R$^2$ are different from an alkoxy group, R$^3$ and R$^4$ are different from an alkoxy group, R$^5$ and R$^6$ are selected from H, Cl, Br, I, —Sn(R$^\circ$)$_3$, —B(OR')(OR"), —CH$_2$Cl, —CHO, —CH=CH$_2$, —SiR$^\circ$R$^{\circ\circ}$R$^{\circ\circ\circ}$ and optionally substituted aryl or heteroaryl, and preferably n is 1, n≧2.

If Ar$^1$ or Ar$^2$ is arylene or heteroarylene, it is preferably a mono-, bi- or tricyclic aromatic or heteroaromatic group with up to 25 C atoms, wherein the rings can be fused, and in which the heteroaromatic group contains at least one hetero ring atom, preferably selected from N, O and S. It is optionally substituted with one or more of F, Cl, Br, I, CN, and straight chain, branched or cyclic alkyl having 1 to 20 C atoms, which is unsubstituted, mono- or, poly-substituted by F, Cl, Br, I, —CN or —OH, and in which one or more non-adjacent CH$_2$ groups are optionally replaced, in each case independently from one another, by —O—, —S—, —NH—, —NR$^\circ$—, —SiR$^\circ$R$^{\circ\circ}$—, —CO—, —COO—, OCO—, —OCO—O, —S—CO—, —CO—S—, —CH=CH— or —C≡C— in such a manner that O and/or S atoms are not linked directly to one another.

Preferred groups arylene or heteroarylene groups are selected from phenyl in which, in addition, one or more CH groups may be replaced by N, or naphthalene, alkyl fluorene or oxazole, wherein all these groups are optionally mono- or polysubstituted with L, wherein L is F, Cl, Br, or an alkyl, alkoxy, alkylcarbonyl, alkylcarbonyloxy or alkoxycarbonyl group with 1 to 12 C atoms, wherein one or more H atoms are optionally replaced by F or Cl. Further preferred groups are thiophene, thienothiophene and dithienothiophene which are substituted by one or more halogen, in particular fluorine, atoms.

Especially preferred arylene or heteroarylene groups are 1,4-phenylene, fluorinated 1,4-phenylene, 2,5-pyridine, 2,5-pyrimidine, p,p'-biphenyl, naphthalene-2,6-diyl, thiophene-2,5-diyl, fluorinated or alkylated thiophene-2,5-diyl, fluorinated benzo[1,2-b:4,5-b']dithiophene, 2,5-thiazole, 2,5-thiadiazole, 2,5-oxazole and 2,5-oxadiazole, all of which are unsubstituted, mono- or polysubstituted with L as defined above.

If one of R$^{1-6}$ is aryl or heteroaryl, it is preferably a mono-, bi- or tricyclic aromatic or heteroaromatic group with up to 25 C atoms, wherein the rings can be fused, and in which the heteroaromatic group contains at least one hetero ring atom, preferably selected from N, O and S. It is optionally substituted with one or more of F, Cl, Br, I, CN, and straight chain, branched or cyclic alkyl having 1 to 20 C atoms, which is unsubstituted, mono- or poly-substituted by F, Cl, Br, I, —CN or —OH, and in which one or more non-adjacent CH$_2$ groups are optionally replaced, in each case independently from one another, by —O—, —S—, —NH—, —NR$^\circ$—, —SiR$^\circ$R$^{\circ\circ}$—, —CO—, —COO—, OCO—, —OCO—O, —S—CO—, —CO—S—, —CH=CH— or —C≡C— in such a manner that O and/or S atoms are not linked directly to one another.

Especially preferred aryl and heteroaryl groups are phenyl, fluorinated phenyl, pyridine, pyrimidine, biphenyl, naphthalene, fluorinated thiophene, benzo[1,2-b:4,5-b']dithiophene, thiazole and oxazole, all of which are unsubstituted, mono- or polysubstituted with L as defined above.

If one of R$^{1-4}$ is an alkyl or alkoxy radical, i.e. where the terminal CH$_2$ group is replaced by —O—, this may be straight-chain or branched. It is preferably straight-chain, has 2 to 8 carbon atoms and accordingly is preferably ethyl, propyl, butyl, pentyl, hexyl, heptyl, octyl, ethoxy, propoxy, butoxy, pentoxy, hexyloxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Fluoroalkyl or fluorinated alkyl or alkoxy is preferably straight chain (O)C$_i$F$_{2i+1}$, wherein i is an integer from 1 to 20, in particular from 1 to 15, very preferably (O)CF$_3$, (O)C$_2$F$_5$, (O)C$_3$F$_7$, (O)C$_4$F$_9$, (O)C$_5$F$_{11}$, (O)C$_6$F$_{13}$, (O)C$_7$F$_{15}$ or (O)C$_8$F$_{17}$, most preferably (O)C$_6$F$_{13}$.

CX$^1$=CX$^2$ is preferably —CH=CH—, —CH=CF—, —CF=CH—, —CF=CF—, —CH=C(CN)— or —C(CN)=CH—.

Halogen is preferably F, Br, Cl or I.

Hetero atoms are preferably selected from N, O and S.

The polymerizable or reactive group P is preferably selected from CH$_2$=CW$^1$—COO—, CH$_2$=CW$^2$—(O)$_{k1}$—, CH$_3$—CH=CH—O—, (CH$_2$=CH)$_2$CH—OCO—, (CH$_2$=CH)$_2$CH—O—, (CH$_2$=CH—CH$_2$)$_2$CH—OCO—, (CH$_2$=CH—CH$_2$)$_2$N—, HO—CW$^2$W$^3$—, HS—CW$^2$W$^3$—, HW$^2$N—, HO—CW$^2$W$^3$—NH—, CH$_2$=CW$^1$—CO—NH—, CH$_2$=CH—(COO)$_{k1}$-Phe-(O)$_{k2}$—, Phe-CH=CH—, HOOC—, OCN—, and W$^4$W$^5$W$^6$Si—, with W$^1$ being H, Cl, CN, phenyl or alkyl with 1 to 5 C-atoms, in particular H, Cl or CH$_3$, W$^2$ and W$^3$ being independently of each other H or alkyl with 1 to 5 C-atoms, in particular methyl, ethyl or n-propyl, W$^4$, W$^5$ and W$^6$ being independently of each other Cl, oxaalkyl or oxacarbonylalkyl with 1 to 5 C-atoms, Phe being 1,4-phenylene and k$_1$ and k$_2$ being independently of each other 0 or 1.

Especially preferred groups P are CH$_2$=CH—COO—, CH$_2$=C(CH$_3$)—COO—, CH$_2$=CH—, CH$_2$=CH—O—, (CH$_2$=CH)$_2$CH—OCO—, (CH$_2$=CH)$_2$CH—O—, and Very preferred are acrylate and oxetane groups. Oxetanes produce less, shrinkage upon polymerization (cross-linking), which results in less stress development within films, leading to higher retention of ordering and fewer defects. Oxetane cross-linking also requires cationic initiator, which unlike free radical initiator is inert to oxygen.

As for the spacer group Sp all groups can be used that are known for this purpose to the skilled in the art. The spacer group Sp is preferably of formula Sp'-X, such that P-Sp- is P-Sp'-X—, wherein Sp' is alkylene with up to 20 C atoms which may be unsubstituted, mono- or poly-substituted by F, Cl, Br, I or CN, it being also possible for one or more non-adjacent CH$_2$ groups to be replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, X is —O—, —S—, —CO—, —COO—, —OCO—, —O—COO—, —CO—NR$^0$—, —NR$^0$—CO—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^0$—, —CX$^1$=CX$^2$—, —C≡C—, —CH=CH—COO—, —OCO—CH=CH— or a single bond, and R$^0$, R$^{00}$, X$^1$ and X$^2$ have one of the meanings given above.

X is preferably —O—, —S—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CX$^1$=CX$^2$—, —C≡C— or a single bond, in particular —O—, —S—, —C≡C—, —CX$^1$=CX$^2$— or a single bond, very preferably a group that is able to from a conjugated system, such as —C≡C— or —CX$^1$=CX$^2$—, or a single bond.

Typical groups Sp' are, for example, —(CH$_2$)$_p$—, —(CH$_2$CH$_2$O)$_q$—CH$_2$CH$_2$—, —CH$_2$CH$_2$—S—CH$_2$CH$_2$— or —CH$_2$CH$_2$—NH—CH$_2$CH$_2$— or —(SiR$^0$R$^{00}$—O)$_p$—, with p being an integer from 2 to 12, q being an integer from 1 to 3 and R$^0$ and R$^{00}$ having the meanings given above.

Preferred groups Sp' are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

Further preferred are compounds with one or two groups P-Sp- wherein Sp is a single bond.

In case of compounds with two groups P-Sp, each of the two polymerizable groups P and the two spacer groups Sp can be identical or different.

SCLCPs obtained from the inventive compounds or mixtures by polymerization or copolymerization have a backbone that is formed by the polymerizable group P.

The mono-, oligo- and polymers of the present invention can be synthesized according to or in analogy to known methods. Some preferred methods are described below.

The key step to the synthesis of all polymers is the preparation of benzodithiophenes containing substituents, preferably alkyl chains, in the 4,8- or 3,7-positions. The preparation of 4,8-dialkyl or otherwise substituted monomer is depicted in Scheme 1 below, wherein R has one of the meanings of R$^1$.

SCHEME I

Firstly 1,4-dialkylbenzene is brominated in the 2,5-positions by treatment with bromine [see H. Kukula; S. Veit; A. Godt, *Eur. J. Org. Chem*, 1999, 277-286]. This is treated with two protected mercapto-ethanal equivalents in the presence of base, and optionally a transition metal catalyst such as Pd(PPh$_3$)$_4$. Examples of protected 2-mercaptoethanals are 2-mercaptomethyl-1,3-dioxolane (HSCH$_2$CH(OCH$_2$CH$_2$O) and 2-mercapto-1,1-dimethoxyethane (HSCH$_2$CH(OCH$_3$)$_2$). Finally the protecting group is removed under acidic conditions and the thiophene ring formed by an acid catalyzed Friedal-Crafts type intramolecular cyclization and subsequent dehydration of the resulting alcohol in situ. This follows procedures similar to those reported for the preparation of 4,8-dimethylbenzodithiophene [see M. Pomerantz; J. Wang; S. Seong; K. P. Starkey; L. Nguyen; D. S. Marynick, *Macromolecules*, 1994, 27, 7478-7485 and P. Beimling; G. Kossmehl, *Chem. Ber.*, 1986, 119, 3198-3203]. The resulting benzodithiophene can be polymerized directly by oxidative coupling with for example ferric (E) chloride. Alternatively the monomer can be brominated in the 2,6-positions and then chemically polymerized to the homopolymer by treatment with Ni(COD)$_2$ (Yamamoto coupling) [see K. Shiraishi; T. Yamamoto, *Synthetic Metals*, 2002, 130, 139-147], the dibromo monomer can also be polymerized by formation of a mono Grignard or organozinc reagent, and treatment of this intermediate with a nickel catalyst (McCullough type polymerization) [see S. M. K. Robert S. Loewe, and; R. D. McCullough*, *Adv. Mater.*, 1999, 11, 250].

The dibromo intermediate can also be used to form co-polymers by co-polymerization with another suitable difunctionalized monomer, such as a bis(boronic) acid or ester, or a di-organotin reagent as demonstrated in Scheme 2, wherein R has one of the meanings of R$^1$ and Ar and n are as defined above.

SCHEME 2

The preparation of 3,7-dialkyl benzodithiophene is depicted in Scheme 3 below, wherein R has one of the meanings of R$^1$, and follows a similar precedent to that described above.

SCHEME 3

Firstly a ketone protected mercaptan such as 7 is prepared as described in the literature [see L. Novak; P. Kolonits; C. Szantay; J. Aszodi; M. Kajtar, *Tetrahedron,* 1982, 38, 153-159]. This is reacted with a 1,4-dibromo-2,5-dichlorobenzene under basic conditions in the presence of a transition metal catalyst to afford dichlorobenzene intermediate 8. The ketal protecting groups are removed under acidic conditions, and the resulting ketone's are cyclized and dehydrated under acidic conditions to afford benzodithiophene intermediate 9 [see R. W. Guthrie; G. L. Kaplan; F. A. Mennona; J. W. Tilley; R. W. Kierstead; M. O'Donnell; H. Crowley; B. Yaremko; A. F. Welton, *J. Med. Chem.,* 1990, 33, 2856-2864]. Finally the chlorine atoms, which are necessary to direct the regiochemistry of the cyclization, are removed by treatment with lithium aluminum hydride. The resulting monomer can be polymerized as described above.

A further aspect of the invention relates to both the oxidized and reduced form of the compounds and materials according to this invention. Either loss or gain of electrons results in formation of a highly delocalized ionic form, which is of high conductivity. This can occur on exposure to common dopants. Suitable dopants and methods of doping are known to those skilled in the art, e.g., from EP 0 528 662, U.S. Pat. No. 5,198,153 or WO 96/21659.

The doping process typically implies treatment of the semiconductor material with an oxidating or reducing agent in a redox reaction to form delocalized ionic centers in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantation of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds and materials of the present invention can be used as an organic "metal" in applications, for example, but not limited to, charge injection layers and ITO planarizing layers in organic light emitting diode applications, films for flat panel displays and touch screens, antistatic films, printed conductive substrates, patterns or tracts in electronic applications such as printed circuit boards and condensers.

A preferred embodiment of the present invention relates to mono-, oligo- and polymers of formula I and its preferred subformulae that are mesogenic or liquid crystalline, and very preferably comprise one or more polymerizable groups. Very preferred materials of this type are monomers and oligomers of formula I and its preferred subformulae wherein n is an integer from 1 to 15 and $R^5$ and/or $R^6$ denote P-Sp-.

These materials are particularly useful as semiconductors or charge transport materials, as they can be aligned into uniform highly ordered orientation in their liquid crystal phase by known techniques, thus exhibiting a higher degree of order that leads to particularly high charge carrier mobility. The highly ordered liquid crystal state can be fixed by in situ polymerization or crosslinking via the groups P to yield polymer films with high charge carrier mobility and high thermal, mechanical and chemical stability.

For example, if a device is made from a polymerizable liquid crystal material by polymerization in situ, the liquid crystal material preferably comprises one or more mono- or oligomers of formula I and its preferred subformulae wherein one or both of $R^5$ and $R^6$ denote P-Sp-. If a liquid crystal polymer is prepared first, for example by polymerization in solution, and the isolated polymer is used to make the device, the polymer is preferably made from a liquid crystal material comprising one or more mono- or oligomers of formula I and its preferred subformulae wherein one of $R^5$ and $R^6$ denotes P-Sp-.

It is also possible to copolymerize the polymerizable mono-, oligo- and polymers according to the present invention with other polymerizable mesogenic or liquid crystal monomers that are known from prior art, in order to induce or enhance liquid crystal phase behavior.

Thus, another aspect of the invention relates to a polymerizable liquid crystal material comprising one or more mono-, oligo- or polymers of the present invention as described above and below comprising at least one polymerizable group, and optionally comprising one or more further polymerizable compounds, wherein at least one of the polymerizable mono-, oligo- and polymers of the present invention and/or the further polymerizable compounds is mesogenic or liquid crystalline.

Particularly preferred are liquid crystal materials having a nematic and/or smectic phase. For FET applications smectic materials are especially preferred. For OLED applications nematic or smectic materials are especially preferred.

Another aspect of the present invention relates to an anisotropic polymer film with charge transport properties obtainable from a polymerizable liquid crystal material as defined above that is aligned in its liquid crystal phase into macroscopically uniform orientation and polymerized or crosslinked to fix the oriented state.

Preferably polymerization is carried out as in-situ polymerization of a coated layer of the material, preferably during fabrication, of the electronic or optical device comprising the inventive semiconductor material. In case of liquid crystal materials, these are preferably aligned in their liquid crystal state into homeotropic orientation prior to polymerization, where the conjugated pi-electron systems are orthogonal to the direction of charge transport. This ensures that the intermolecular distances are minimized and hence then energy required to transport charge between molecules is minimized. The molecules are then polymerized or crosslinked to fix the uniform orientation of the liquid crystal state. Alignment and curing are carried out in the liquid crystal phase or mesophase of the material. This technique is known in the art and is generally described for example in D. J. Broer, et al., *Angew. Makromol. Chem.* 183, (1990), 45-66.

Alignment of the liquid crystal material can be achieved for example by treatment of the substrate onto which the material is coated, by shearing the material during or after coating, by application of a magnetic or electric field to the coated material, or by the addition of surface-active compounds to the liquid crystal material. Reviews of alignment techniques are given for example by I. Sage in "Thermotropic Liquid Crystals," edited by G. W. Gray, John Wiley & Sons, 1987, pages 75-77, and by T. Uchida and H. Seki in "Liquid Crystals—Applications and Uses Vol. 3," edited by B. Bahadur, World Scientific Publishing, Singapore 1992, pages 1-63. A review of alignment materials and techniques is given by J. Cognard, *Mol. Cryst. Liq. Cryst.* 78, Supplement 1 (1981), pages 1-77.

Polymerization takes place by exposure to heat or actinic radiation. Actinic radiation means irradiation with light, like UV light, IR light or visible light, irradiation with X-rays or gamma rays or irradiation with high energy particles, such as ions or electrons. Preferably polymerization is carried out by UV irradiation at a non-absorbing wavelength. As a source for actinic radiation for example a single UV lamp or a set of UV lamps can be used. When using a high lamp power the curing time can be reduced. Another possible source for actinic radiation is a laser, like e.g. a UV laser, an IR laser or a visible laser.

Polymerization is preferably carried out in the presence of an initiator absorbing at the wavelength of the actinic radiation. For example, when polymerizing by means of UV light, a photoinitiator can be used that decomposes under UV irradiation to produce free radicals or ions that start the polymerization reaction. When curing polymerizable materials with acrylate or methacrylate groups, preferably a radical photoinitiator is used, when curing polymerizable materials with vinyl, epoxide and oxetane groups, preferably a cationic photoinitiator is used. It is also possible to use a polymerization initiator that decomposes when heated to produce free radicals or ions that start the polymerization. As a photoinitiator for radical polymerization for example the commercially available Irgacure 65-1, Irgacure 184, Darocure 1173 or Darocure 4205 (all from Ciba Geigy AG) can be used, whereas in case of cationic photopolymerization the commercially available UVI 6974 (Union Carbide) can be used.

The polymerizable material can additionally comprise one or more other suitable components such as, for example, catalysts, sensitizers, stabilizers, inhibitors, chain-transfer agents, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colorants, dyes or pigments.

Mono-, oligo- and polymers comprising one or more groups P-Sp- can also be copolymerized with polymerizable mesogenic compounds to induce or enhance liquid crystal phase behavior. Polymerizable mesogenic compounds that are suitable as comonomers are known in prior art and disclosed for example in WO 93/22397; EP 0,261,712; DE 195, 04,224; WO 95/22586 and WO 97/00600.

Another aspect of the invention relates to a liquid crystal side chain polymer (SCLCP) obtained from a polymerizable liquid crystal, material as defined above by polymerization or polymeranalogous reaction. Particularly preferred are SCLCPs obtained from one or more monomers of formula I1 and its preferred subformulae wherein one or both, preferably one, of $R^5$ and $R^6$ are a polymerizable or reactive group, or from a polymerizable mixture comprising one or more of said monomers.

Another aspect of the invention relates to an SCLCP obtained from one or more monomers of formula I1 and its preferred subformulae wherein one or both of $R^5$ and $R^6$ are a polymerizable group, or from a polymerizable liquid crystal mixture as defined above, by copolymerization or polymeranalogous reaction together with one or more additional mesogenic or non-mesogenic comonomers.

Side chain liquid crystal polymers or copolymers (SCLCPs), in which the semiconducting component is located as a pendant group, separated from a flexible backbone by an aliphatic spacer group, offer the possibility to obtain a highly ordered lamellar like morphology. This structure consists of closely packed conjugated aromatic mesogens, in which very close (typically <4 Å) pi-pi stacking can occur. This stacking allows intermolecular charge transport to occur more easily, leading to high charge carrier mobilities. SCLCPs are advantageous for specific applications as they can be readily synthesized before processing and then e.g. be processed from solution in an organic solvent. If SCLCPs are used in solutions, they can orient spontaneously when coated onto an appropriate surface and when at their mesophase temperature, which can result in large area, highly ordered domains.

SCLCPs can be prepared from the polymerizable compounds or mixtures according to the invention by the methods described above, or by conventional polymerization techniques which are known to those skilled in the art, including for example radicalic, anionic or cationic chain polymerization, polyaddition or polycondensation. Polymerization can be carried out for example as polymerization in solution, without the need of coating and prior alignment, or polymerization in situ. It is also possible to form SCLCPs by grafting compounds according to the invention with a suitable reactive group, or mixtures thereof, to presynthesized isotropic or anisotropic polymer backbones in a polymeranalogous reaction. For example, compounds with a terminal hydroxy group can be attached to polymer backbones with lateral carboxylic acid or ester groups, compounds with terminal isocyanate groups can be added to backbones with free hydroxy groups, compounds with terminal vinyl or vinyloxy groups can be added, e.g., to polysiloxane backbones with Si—H groups. It is also possible to form SCLCPs by copolymerization or polymeranalogous reaction from the inventive compounds together with conventional mesogenic or non mesogenic comonomers. Suitable comonomers are known to those skilled in the art. In principle it is possible to use all conventional comonomers known in the art that carry a reactive or polymerizable group capable of undergoing the desired polymer-forming reaction, like for example a polymerizable or reactive group P as defined above. Typical mesogenic comonomers are for example those mentioned in WO 93/22397, EP 0 261 712, DE 195 04 224, WO 95/22586, WO 97/00600 and GB 2 351 734. Typical non mesogenic comonomers are for example alkyl acrylates or alkyl methacrylates with alkyl groups of 1 to 20 C atoms, like methyl acrylate or methyl methacrylate.

The mono-, oligo- and polymers of the present invention are useful as optical, electronic and semiconductor materials, in particular as charge transport materials in field effect transistors (FETs), e.g., as components of integrated circuitry, ID tags or TFT applications. Alternatively, they may be used in organic light emitting diodes (OLEDs) in electroluminescent display applications or as backlight of, e.g., liquid crystal displays, as photovoltaics or sensor materials, for electrophotographic recording, and for other semiconductor applications.

Especially the oligomers and polymers according to the invention show advantageous solubility properties which allow production processes using solutions of these compounds. Thus films, including layers and coatings, may be generated by low cost production techniques, e.g., spin coating. Suitable solvents or solvent mixtures comprise alkanes and/or aromatics, especially their fluorinated derivatives.

The materials of the present invention are useful as optical, electronic and semiconductor materials, in particular as charge transport materials in field effect transistors (FETs), as photovoltaics or sensor materials, for electrophotographic recording, and for other semiconductor applications. Such FETs, where an organic semiconductive material is arranged as a film between a gate-dielectric and a drain and a source electrode, are generally known, e.g., from U.S. Pat. No. 5,892,244, WO 00/79617, U.S. Pat. No. 5,998,804, and from the references cited in the background and prior art chapter and listed below. Due to the advantages, like low cost production using the solubility properties of the compounds according to the invention and thus the processibility of large surfaces, preferred applications of these FETs are such as integrated circuitry, TFT-displays and security applications.

In security applications, field effect transistors and other devices with semiconductive materials, like transistors or diodes, may be used for ID tags or security markings to authenticate and prevent counterfeiting of documents of value like banknotes, credit cards or ID cards, national ID documents, licenses or any product with monetary value, like stamps, tickets, shares, checks etc.

Alternatively, the mono-, oligo- and polymers according to the invention may be used in organic light emitting devices or diodes (OLEDs), e.g., in display applications or as backlight of e.g. liquid crystal displays. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Meerholz, *Synthetic Materials*, 111-112, 2000, 31-34, Alcala, *J. Appl. Phys.*, 88, 2000, 7124-7128 and the literature cited therein.

According to another use, the inventive compounds, materials or films, especially those which show photoluminescent properties, may be employed as materials of light sources, e.g., of display devices such as described in EP 0 889 350 A1 or by C. Weder et al., *Science*, 279, 1998, 835-837.

According to another use, the inventive compounds, materials or films can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarization charge of the ferroelectric LCs. When used in an OLED device comprising a light emitting material provided onto the alignment layer, this increased electrical conductivity can enhance the electroluminescence of the light emitting material. The compounds or materials according to the present invention having mesogenic or liquid crystalline properties can form oriented anisotropic films as described above, which are especially useful as alignment layers to induce or enhance alignment in a liquid crystal medium provided onto said anisotropic film. The materials according to the present invention may also be combined with photoisomerizable compounds and/or chromophores for use in or as photoalignment layers, as described in US 2003/0021913.

According to another use the polymers according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, *Proc. Natl. Acad. Sci.* U.S.A. 1999, 96, 12287; D. Wang, X. Gong, P. S. Heeger, F. Rininsland, G. C. Bazan and A. J. Heeger, *Proc. Natl. Acad. Sci.* U.S.A. 2002, 99, 49; N. DiCesare, M. R. Pinot, K. S. Schanze and J. R. Lakowicz, *Langmuir* 2002, 18, 7785; D. T. McQuade, A. E. Pullen, T. M. Swager, *Chem. Rev.* 2000, 100, 2537.

The examples below serve to illustrate the invention without limiting it. In the foregoing and the following, all temperatures are given in degrees Celsius, and all percentages are by weight, unless stated otherwise.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLE 1

Poly-(4,8-dihexylbenzo[1,2-b;4,5-b']dithiophene) (1d) is prepared as shown in Scheme 1 above.

1a) Sodium [1,3]dioxolan-2-ylmethanethiolate

2-Bromomethyl[1,3]dioxolane (101.2 g, 0.606 mol) and potassium thioacetate (70.8 g, 0.620 mol) in DMF (700 mL) are stirred at 40° C. for 70 h under nitrogen. The reaction mixture is cooled to RT and filtered. The solvent is removed under reduced pressure. The residue is dissolved in DCM (400 mL) and washed with water (400 mL). The aqueous layer is extracted again with DCM (2×100 mL). The combined extracts are washed with brine (2×100 mL), dried over sodium sulfate, and concentrated in vacuo. The residue is filtered through silica (eluent: DCM) and concentrated in vacuo to afford thioacetic acid S-[1,3]dioxolan-2-ylmethyl ester (97.1 g, 99%). Thioacetic acid S-[1,3]dioxolan-2-ylmethyl ester (63.4 g, 0.391 mol) and sodium methoxide (21.6 g, 0.400 mol) in anhydrous methanol (1 L) are stirred at RT for 12 h. The solvent is removed under reduced pressure to yield the product as a yellow solid (37.5 g, 67%): $^1$H NMR as expected.

1b) 2,5-Bis([1,3]dioxolan-2-ylmethanethiolato)-1,4-dihexylbenzene

A 3-necked flask is charged with sodium [1,3]dioxolan-2-ylmethanethiolate (1.78 g, 12.50 mmol) and sodium tert-butoxide (1.20 g, 12.5 mmol) and purged with nitrogen. Anhydrous toluene (30 mL) is added and the reaction mixture is stirred at RT overnight. Palladium(II) acetate (0.11 g, 0.50 mmol), rac-BINAP (0.34 g, 0.55 mmol) and 2,5-dibromo-1,4-dihexylbenzene (2.02 g, 5.00 mmol) are added and the reaction mixture is stirred at 80° C. for 24 h. The reaction mixture is cooled to RT and diluted with EtOAc (100 mL). Water (100 mL) is added. The organic extract is collected. The aqueous layer is extracted again with EtOAc (100 mL). The combined extracts are washed with water (2×100 mL), dried over sodium sulfate, and concentrated in vacuo. Column chromatography (eluent: 50% DCM/50% petrol) yielded the product as a pale yellow oil (0.90 g, 37%): $^1$H NMR (CDCl$_3$, 300 MHz): δ 7.18 (s, 2H, ArH), 5.08 (t, $^3$J=4.5 Hz, 2H, OCHO), 4.03 (m, 4H, OCH$_2$), 3.89 (m, 4H, OCH$_2$), 3.08 (d, $^3$J=4.5 Hz, 4H, SCH$_2$), 2.70 (t, $^3$J=8.0 Hz, 4H, ArCH$_2$), 1.57 (m, 4H, CH$_2$), 1.29 (br, 12H, CH$_2$), 0.88 (t, $^3$J=6.5 Hz, 2H, CH$_3$).

1c) 4,8-Dihexylbenzo[1,2-b;4,5-b']dithiophene

A solution of 2,5-bis([1,3]dioxolan-2-ylmethanethiolato)-1,4-dihexylbenzene (0.48 g, 1.00 mmol) in chlorobenzene (5 mL) is added dropwise to a refluxing solution of 84% polyphosphoric acid (0.5 mL) in chlorobenzene (5 mL) under nitrogen. The reaction mixture is stirred at reflux for 60 h. After cooling to RT, the reaction mixture is poured into water (100 mL) and extracted into DCM (2×100 mL). The combined extracts are washed with water (100 mL), dried over sodium sulfate and concentrated in vacuo. Column chromatography (eluent: petroleum ether 40-60) yielded the product as a pale yellow solid (0.25 g, 69%): $^1$H NMR (CDCl$_3$, 300 MHz): δ 7.48 (d, J=5.5 Hz, 2H, Arm, 7.45 (d, J=5.5 Hz, 2H, Arm, 3.18 (t, $^3$J=8.0 Hz, 4H, ArCH$_2$), 1.81 (m, 4H, CH$_2$), 1.48 (m, 4H, CH$_2$), 1.34 (br, 8H, CH$_2$), 0.90 (t, J=6.5 Hz, 6H, CH$_3$).

1d) Poly(4.8-dihexylbenzo[1,2-b;4,5-b']dithiophene)

A solution of 4,8-dihexylbenzo[1,2-b;4,5-b']dithiophene (0.20 g, 0.55 mmol) in anhydrous CHCl$_3$ (10 mL) is added to a stirred solution of anhydrous FeCl$_3$ (0.45 g, 2.75 mmol) in anhydrous CHCl$_3$ (40 mL) in a 3-necked flask fitted with a condenser. The reaction mixture is stirred for 20 h at RT with a constant flow of nitrogen bubbled into the reaction mixture to remove HCl formed. The reaction mixture is poured into methanol (300 mL) and stirred for 1 h. The polymer is collected by filtration and washed with water followed by methanol. The polymer is de-doped by stirring in conc. NH$_4$OH (50 mL, 33%) for 1 h. The precipitate is collected by filtration, washed with water followed by methanol, and dried under vacuum. The polymer is washed (via Soxhlet extraction) with methanol for 21 h and petroleum ether 40-60 for 5 h. before being dried under vacuum to yield the product as a dark red solid (0.15 g, 75%).

EXAMPLE 2

Poly-(4,8-didecylbenzo[1,2-b;4,5-b']dithiophene) (2d) is prepared as shown in Scheme 1 above.

2a) 2.5-Dibromo-, 1,4-didecylbenzene 2,5-Dibromo-1,4-didecylbenzene is prepared from 1,4-dibromobenzene in two steps according to literature procedures: decylmagnesium bromide is coupled to 1,4 dibromobenzene using PdCl$_2$(dppf) to yield 1,4-didecylbenzene, which is subsequently treated with bromine to afford 2,5-dibromo-1,4-didecylbenzene.

2b) 2,5-Bis([1,3]dioxolan-2-ylmethanethiolato)-1,4-didecylbenzene

A 3-necked flask is charged with sodium [1,3]dioxolan-2-ylmethanethiolate (2.84 g, 20.00 mmol) and sodium tert-butoxide (2.31 g, 20.00 mmol) and purged with nitrogen. Anhydrous toluene (50 mL) is added and the reaction mixture is stirred at RT overnight. Palladium(II) acetate (0.18 g, 0.80 mmol), rac-BINAP (0.55 g, 0.88 mmol) and 2,5-dibromo-1,4-didecylbenzene (4.13 g, 8.00 mmol) are added and the reaction mixture is stirred at 80° C. for 48 h. The reaction mixture is cooled to RT and diluted with EtOAc (200 mL). Water (100 mL) is added. The organic extract is collected. The aqueous layer is extracted again with EtOAc (200 mL). The combined extracts are washed with water (2×100 mL), dried over sodium sulfate, and concentrated in vacuo. Column chromatography (eluent: 50% DCM/50% petrol) yielded product as a pale yellow oil (3.20 g, 67%): $^1$H NMR as expected.

2c) 4.8-Didecylbenzo[1,2-b;4,5-b']dithiophene

A solution of 2,5-bis([1,3]dioxolan-2-ylmethanethiolato)-1,4-didecylbenzene (3.00 g, 5.04 mmol) in chlorobenzene (25 mL) is added dropwise to a refluxing solution of 84% polyphosphoric acid (3 m L) in chlorobenzene (25 mL) under nitrogen. The reaction mixture is stirred at reflux for 7 days. After cooling to RT, the reaction mixture is poured into water (200 mL) and extracted into DCM (2×200 mL). The combined extracts are washed with water (100 mL), dried over sodium sulfate and concentrated in vacuo. Column chromatography (eluent: petroleum ether 40-60) yielded the product as a pale yellow solid (0.60 g, 25%): $^1$H NMR as expected.

2d) Poly(4,8-didecylbenzo[1,2-b;4,5-b']dithiophene) via oxidative polymerization A solution of 4,8-didecylbenzo[1,2-b;4,5-b']dithiophene (0.30 g, 0.64 mmol) in anhydrous CHCl$_3$ (10 mL) is added to a stirred solution of anhydrous FeCl$_3$ (0.60 g, 3.69 mmol) in anhydrous CHCl$_3$ (40 mL) in a 3-necked flask fitted with a condenser. The reaction mixture is stirred for 48 h at RT with a constant flow of nitrogen bubbled into the reaction mixture to remove HCl formed. The reaction mixture is poured into methanol (300 mL) and stirred for 1 h. The polymer is collected by filtration and washed with water followed by methanol. The polymer is de-doped by stirring in conc. NH$_4$OH (50 mL, 33%) for 1 h. The precipitate is collected by filtration, washed with water followed by methanol, and dried under vacuum. The polymer is washed (via Soxhlet extraction) with methanol for 18 h and petroleum ether 40-60 for 6 h. before being dried under vacuum to yield the product as a dark red solid (0.21 g, 70%).

2e) 2,6-Dibromo-4,8-didecylbenzo[1,2-b;4,5-b']dithiophene

NBS (0,89 g, 5.00 mmol) is added to a solution of 4,8-didecylbenzo[1,2-b;4,5-b']dithiophene (1.16 g, 2.46 mmol) in CHCl$_3$ (10 mL) and AcOH (10 mL) under nitrogen. The reaction mixture is stirred at RT for 27 h. The reaction mixture is poured into water (50 mL) and extracted into DCM (2×100 mL). The combined extracts are washed with water (50 mL), dried over sodium sulfate, and concentrated in vacuo. Recrystallization twice from acetone afforded the product as pale yellow needles (0.80 g, 53%): $^1$H NMR (CDCl$_3$, 300 MHz): δ 7.41 (s, 2H, ArH), 2.98 (t, $^3$J=8.0 Hz, 4H, ArCH$_2$), 1.73 (m, 4H, CH$_2$), 1.33 (br, 28H, CH$_2$), 0.88(t, $^3$J=6.5 Hz, 6H, CH$_3$).

2d) Poly(4.8-didecylbenzo[1,2-b;4,5-b']dithiophene) via Yamamoto coupling

A schlenk tube is charged with Ni(cod)$_2$ (0.26 g, 0.93 mmol) and bipy (0.15 g, 0.93 mmol) under nitrogen. cod (0.10 mL, 0.80 mmol) and anhydrous DMF (3 mL) are added. The reaction mixture is stirred at 60° C. for 30 minutes. A solution of 2,6-dibromo-4,8-didecylbenzo[1,2-b;4,5-b']dithiophene (0.42 is 0.66 mmol) in anhydrous toluene (9 mL) is added. The reaction mixture is stirred at 80° C. for 24 h. Bromobenzene (0.2 mL) is added and the reaction mixture is stirred at 80° C. for 1 h. After cooling to RT, the reaction mixture is precipitated into acidic methanol (300 mL) and stirred for 0.5 h. The precipitate is collected by filtration, washed with methanol, and dried under vacuum. The polymer is washed (via Soxhlet extraction) with methanol for 20 h and petroleum ether 40-60 for 6 h. before being dried under vacuum to yield the product as a dark red solid (0.33 g, 96%).

The entire disclosure of all applications, patents and publications, cited herein and of corresponding European application No. 03023339.9, filed Oct. 15, 2003, is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An oligo- or polymer comprising in its backbone 3 to 5000 identical or different recurring benzodithiophene-2,6-diyl groups, which are, each independently, substituted in 3- and 7- position and/or in 4- and 8-position, with the proviso that oligo- and poly(4,8-bisalkoxybenzodithiophenes) are excluded.

2. An oligo- or polymer, comprising in its backbone 3 to 5000 identical or different recurring units of formula I

I wherein

R$^1$ to R$^4$ are, independently of each other, H, halogen or straight chain, branched or cyclic alkyl with 1 to 20 C-atoms, which is unsubstituted, mono- or poly-substituted by F, Cl, Br, I or CN, in which optionally one or more non-adjacent CH$_2$ groups are replaced, in each case independently from one another, by —O—, —S—, —NH—, —NR$^o$—, —SiR$^o$R$^{oo}$—, —CO—, —COO—, —OCO—, —OCO—O—, —S—CO—, —CO—S—, —CH=CH— or —C≡C— in such a manner that O and/or S atoms are not linked directly to one another, or optionally substituted aryl or heteroaryl, or P-Sp-, P is a polymerizable or reactive group, Sp is a spacer group or a single bond, $R^0$ and $R^{00}$ are, independently of each other, H or alkyl with 1 to 12 C-atoms,

$Ar^1$ and $Ar^2$ are, independently of each other, $-CX^1=CX^2-$, $-C\equiv C-$, an arylene or heteroarylene group that is optionally substituted with one or more groups $R^1$, or a single bond, $X^1$ and $X^2$ are, independently of each other, H, F, Cl or CN, with the provisos that a) in at least one recurring unit $R^1$ to $R^2$ are different from H and/or $R^3$ and $R^4$ are different from H, and b) $R^1$ to $R^2$ do not at the same time denote alkoxy groups.

3. An oligo- or polymer, comprising in its backbone a unit of formula I1 wherein n is 3 to 5000, whereby 3 to 5000 recurring units of the structure in the brackets are present in a unit of formula I1 in the backbone of the oligo- or polymer, and wherein said 3 to 5000 recurring units may be identical or different, $R^1$ to $R^4$ are, independently of each other, H, haloaen or straight chain, branched or cyclic alkyl with 1 to 20 C-atoms, which is unsubstituted, mono- or poly-substituted by F, Cl, Br, I or CN, in which optionally one or more non-adjacent $CH_2$ groups are replaced, in each case independently from one another, by $-O-$, $-S-$, $-NH-$, $-NR^0-$, $-SiR^0R^{00}-$, $-CO-$, $-COO-$, $-OCO-$, $-OCO-O-$, $-S-CO-$, $-CO-S-$, $-CH=CH-$ or $-C\equiv C-$ in such a manner that O and/or S atoms are not linked directly to one another, or optionally substituted aryl or heteroaryt, or P-Sp-, P is a polymerizable or reactive group, Sp is a spacer group or a single bond, $R^0$ and $R^{00}$ are, independently of each other, H or alkyl with 1 to 12 C-atoms,

$Ar^1$ and $Ar^2$ are, independently of each other, $-CX^1=CX^2-$, $-C\equiv C-$, an arylene or heteroarylene group that is optionally substituted with one or more groups $R^1$, or a single bond, $X^1$ and $X^2$ are, independently of each other, H, F, Cl or CN, with the provisos that a) in at least one recurring unit $R^1$ to $R^2$ are different from H and/or $R^3$ and $R^4$ are different from H, and b) $R^1$ to $R^2$ do not at the same time denote alkoxy groups.

4. An oligo- or polymer of formula I1a wherein n is 3 to 5000, whereby 3 to 5000 recurring units of the structure in the brackets are present in the oligo- or polymer of formula I1a, and wherein said 3 to 5000 recurring units may be identical or different, $R^5$ and $R^6$ are, independently of each other, H, halogen, $-Sn(R^0)_3$, $-B(OR')(OR'')$, $-CH_2Cl$, $-CHO$, $-CH=CH_2$, $-SiR^0R^{00}R^{000}$, optionally substituted aryl or heteroaryl or P-Sp-, or alkyl with 1 to 12 C-atoms, $R^0$, $R^{00}$ and $R^{000}$ are, independently of each other, H or alkyl with 1 to 12 C-atoms, R' and R" are, independently of each other, H or alkyl with 1 to 12 C-atoms, or OR' and OR" together with the boron atom form a cyclic group having 2 to 20 C atoms, P is a polymerizable or reactive group, Sp is a spacer group or a single bond, $R^1$ to $R^4$ are, independently of each other, H, halogen or straight chain, branched or cyclic alkyl with 1 to 20 C-atoms, which is unsubstituted, mono- or poly-substituted substituted by F, Cl, Br, I or CN, in which optionally one or more non-adjacent $CH_2$ groups are replaced, in each case independently from one another, by $-O-$, $-S-$, $-NH-$, $-NR^0-$, $-SiR^0R^{00}-$, $-CO-$, $-COO-$, $-OCO-$, $-OCO-O-$, $-S-CO-$, $-CO-S-$, $-CH=CH-$ or $-C\equiv C-$ in such a manner that O and/or S atoms are not linked directly to one another, or optionally substituted aryl or heteroaryl, or P-Sp-, $Ar^1$ and $Ar^2$ are, independently of each other, $-CX^1=CX^2-$, $-C\equiv C-$, an arylene or heteroarylene group that is optionally substituted with one or more groups $R^1$, or a single bond, and $X^1$ and $X^2$ are, independently of each other, H, F, Cl or CN, with the provisos that a) in at least one recurring unit $R^1$ to $R^2$ are different from H and/or $R^3$ and $R^4$ are different from H, and b) $R^1$ to $R^2$ do not at the same time denote alkoxy groups.

5. An oligo- or polymer according to claim 1, wherein the number of recurring units is 10 to 5000.

6. An oligo- or polymer according to claim 4, wherein $R^5$ and $R^6$ are, each independently, H, Cl, Br, I, $-Sn(R^0)_3$, $-B(OR'(OR'')$, $-CH_2Cl$, $-CHO$, $-CH=CH_2$, $-SiR^0R^{00}R^{000}$ or P-Sp-.

7. An oligo- or polymer according to claim 2, wherein $R^1$ and $R^2$ are, each independently, $C_1$-$C_{20}$-alkyl that is optionally substituted with one or more fluorine atoms, $C_1$-$C_{20}$-alkenyl, $C_1$-$C_{20}$-alkynyl, $C_1$-$C_{20}$-thioether, $C_1$-$C_{20}$-silyl, $C_1$-$C_{20}$-ester, $C_1$-$C_{20}$-amino, $C_1$-$C_{20}$-fluoroalkyl or optionally substituted aryl or heteroaryl, and $R^3$ and $R^4$ are H.

8. An oligo- or polymer according to claim 2, wherein $R^3$ and $R^4$ are, each independently, $C_1$-$C_{20}$-alkyl that is optionally substituted with one or more fluorine atoms, $C_1$-$C_{20}$-alkenyl, $C_1$-$C_{20}$-alkynyl, $C_1$-$C_{20}$-thioether, $C_1$-$C_{02}0$-silyl, $C_1$-$C_{20}$-ester, $C_1$-$C_{20}$-amino, $C_1$-$C_{20}$-fluoroalkyl or optionally substituted aryl or heteroaryl, and $R^1$ and $R^2$ are H.

9. An oligo- or polymer according to claim 2, wherein $Ar^1$ and/or $Ar^2$ is phenyl in which one or more OH groups may be replaced by N, or naplithalene, alIcyl fluorene or oxazole, each optionally mono- or polysubstituted with L, wherein L is F, Cl, Br, or an alkyl, alkoxy, alkylcarbonyl, alkylcarbonyloxy or alkoxycarbonyl group with 1 to 12 C atoms, wherein one or more H atoms are optionally replaced by F or Cl, or thiophene, thienothiophene or dithienothiophene which are substituted by one or more halogen atoms.

10. An oligo- or polymer according to claim 2, wherein $Ar^1$ and/or $Ar^2$ is a single bond.

11. A polymerizable liquid crystal material comprising one or more oligo- or polymers according to claim 1, comprising at least one polymerizable group, and optionally comprising one or more further polymerizable compounds, wherein at least one of the one or more oligo- or polymers or one or more further polymerizable compounds is mesogenic or liquid crystalline.

12. An anisotropic polymer film with charge transport properties obtainable from a polymerizable liquid crystal material according to claim 11 that is aligned in its liquid crystal phase into macroscopically uniform orientation and polymerized or crosslinked to fix the oriented state.

13. In a semiconductor or charge transport material in an optical, electrooptical or electronic device, or in a field effect transistor (FET), in an integrated circuitry, in a thin film transistors (TFT) for a flat panel display application, or in a radio frequency identification (RFID) tag, or in a semiconducting component for a display or in an organic light emitting diode (OLED) application, in a charge transport and/or electroluminescent layer, the improvement, comprising A) one or more oligo- or polymers according to claim 1, or B) a polymerizable material comprising one or more oligo- or polymers according to claim 1, which comprises at least one polymerizable group, and optionally comprising one or more further polymerizable compounds, wherein at least one of the one or more oligo- or polymers or one or more further polymerizable compounds is mesogenic or liquid crystalline.

14. In an electroluminescent material, for OLED applications, for an electroluminescent display or backlight of a display, in a photovoltaic or sensor device, as an electrode material in a battery, as a photoconductor, for an electrophotographic application, for electrophotographic recording, for an organic memory device, for detecting and discriminating DNA sequences, or as alignment layer in an LCD or OLED device, the improvement, comprising A) one or more oligo- or polymers according to claim 1, or B) a polymerizable material comprising one or more oligo- or polymers according to claim 1, which comprises at least one polymerizable group, and optionally comprising one or more further polymerizable compounds, wherein at least one of the one or more oligo- or polymers or one or more further polymerizable compounds is mesogenic or liquid crystalline.

15. In an optical, electrooptical or electronic device, FET, integrated circuit (IC), TFT, OLED or alignment layer, the improvement, comprising A) one or more oligo- or polymers according to claim 1, or B) a polymerizable material comprising one or more oligo- or polymers according to claim 1, which comprises at least one polymerizable group, and optionally comprising one or more further polymerizable compounds, wherein at least one of the one or more oligo- or polymers or one or more further polymerizable compounds is mesogenic or liquid crystalline.

16. In a TFT or TFT array for a flat panel display, radio frequency identification (RFID) tag, electroluminescent display or backlight the improvement, comprising A) one or more oligo- or polymers according to claim 1, or B) a polymerizable material comprising one or more oligo- or polymers according to claim 1, which comprises at least one polymerizable group, and optionally comprising one or more further polymerizable compounds, wherein at least one of the one or more oligo- or polymers or one or more further polymerizable compounds is mesogenic or liquid crystalline.

17. In a security marking or device comprising a FET or an RFID tag, the improvement, comprising A) one or more oligo- or polymers according to claim 1, or B) a polymerizable material comprising one or more oligo- or polymers according to claim 1, which comprises at least one polymerizable group, and optionally comprising one or more further polymerizable compounds, wherein at least one of the one or more oligo- or polymers or one or more further polymerizable compounds is mesogenic or liquid crystalline.

18. A conducting ionic material, comprising A) one or more oligo- or polymers according to claim 1, or B) a polymerizable material comprising one or more oligo- or polymers according to claim 1, which comprises at least one polymerizable group, and optionally comprising one or more further polymerizable compounds, wherein at least one of the one or more oligo- or polymers or one or more further polymerizable compounds is mesogenic or liquid crystalline.

19. A charge injection layer, planarizing layer, antistatic film or conducting substrate or pattern for an electronic application or flat panel display, comprising a conducting ionic material according to claim 18.

20. An oligo- or polymer according to claim 2, wherein the number of recurring units is 10 to 5000.

21. An oligo- or polymer according to claim 4, wherein $R^5$ and $R^6$ are, independently of each other, H, halogen, —Sn($R^0$)$_3$, —B(OR')(OR''), —CH$_2$Cl, —CHO, —CH=CH$_2$, —SiR$^0$R$^{00}$R$^{000}$, option ally substituted aryl or heteroaryl or P-Sp-.

22. In a FET, IC, TFT or OLED, the improvement, comprising A) one or more oligo- or polymers according to claim 1, or B) a polymerizable material comprising one or more oligo- or polymers according to claim 1, which comprises at least one polymerizable group, and optionally comprising one or more further polymerizable compounds, wherein at least one of the one or more oligo- or polymers or one or more further polymerizable compounds is mesogenic or liquid crystalline.

23. An oligo- or polymer according to claim 1, wherein the number of recurring units is 5 to 5000.

24. An oligo- or polymer according to claim 2, wherein the number of recurring units is 5 to 5000.

* * * * *

UNITED STATES PATENT AND TRADEMARK OFFICE
CERTIFICATE OF CORRECTION

PATENT NO. : 7,524,922 B2
APPLICATION NO. : 10/963720
DATED : April 28, 2009
INVENTOR(S) : Martin Heeney It is certified that error appears in the above-identified patent and that said Letters Patent is hereby corrected as shown below:

Column 23, line 40 reads "$R^1$ to $R^4$ are, independently of each other, H, haloaen or" should read -- $R^1$ to $R^4$ are, independently of each other, H, halogen or --

Column 23, line 51 reads "optionally substituted aryl or heteroaryt, or P-Sp-," should read -- optionally substituted aryl or heteroaryl, or P-Sp-, --

Column 25, line 4 reads "and/or $Ar^2$ is phenyl in which one or more OH groups may be" should read -- and/or $Ar^2$ is phenyl in which one or more CH groups may be --

Column 25, line 5 reads "replaced by N, or naplithalene, a1lcyl fluorine or oxazole," should read -- replaced by N, or naphthalene, alkyl fluorine or oxazole, --

Column 26, line 9, reads "play or backlight the improvement, comprising A) on or" should read -- play or backlight, the improvement, comprising A) on or --

Column 26, line 43, reads "–$CH=CH_2$, –$SiR^0R^{00}R^{000}$, option ally substituted" should read -- –$CH=CH_2$, –$SiR^0R^{00}R^{000}$, optionally substituted --

Signed and Sealed this

Thirtieth Day of June, 2009

JOHN DOLL
*Acting Director of the United States Patent and Trademark Office*